(12) United States Patent
Groot et al.

(10) Patent No.: US 10,399,956 B2
(45) Date of Patent: Sep. 3, 2019

(54) METHOD FOR MANUFACTURING LACTIDE

(71) Applicant: PURAC BIOCHEM B.V., Gorinchem (NL)

(72) Inventors: Wim Jacob Groot, Gorinchem (NL); Jan Van Krieken, Gorinchem (NL); Tanja Dekic Zivkovic, Gorinchem (NL); Andre Banier De Haan, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 15/550,079

(22) PCT Filed: Feb. 11, 2016

(86) PCT No.: PCT/EP2016/052888
§ 371 (c)(1),
(2) Date: Aug. 10, 2017

(87) PCT Pub. No.: WO2016/128501
PCT Pub. Date: Aug. 18, 2016

(65) Prior Publication Data
US 2018/0030025 A1 Feb. 1, 2018

(30) Foreign Application Priority Data
Feb. 13, 2015 (EP) .................... 15155011

(51) Int. Cl.
*C07D 319/12* (2006.01)

(52) U.S. Cl.
CPC .................. *C07D 319/12* (2013.01)

(58) Field of Classification Search
CPC .................................. C07D 319/12
See application file for complete search history.

(56) References Cited

U.S. PATENT DOCUMENTS

| 2,710,880 A | 6/1955 | Filachione et al. |
| 5,274,073 A * | 12/1993 | Gruber .................. C08G 63/08 525/415 |
| 5,319,107 A * | 6/1994 | Benecke .............. C07D 319/12 549/274 |
| 5,420,304 A | 5/1995 | Verser et al. |
| 2009/0093034 A1 | 4/2009 | Uyama et al. |
| 2011/0155557 A1 | 6/2011 | Coszach et al. |
| 2012/0116100 A1 | 5/2012 | Kamikawa et al. |

FOREIGN PATENT DOCUMENTS

| GB | 173 479 A | 11/1922 | |
| GB | 280 969 A | 6/1928 | |
| JP | H09-500649 A | 1/1997 | |
| WO | 95/03268 A1 | 2/1995 | |
| WO | 00/017378 A2 | 3/2000 | |
| WO | WO-0043381 A1 * | 7/2000 | ........... C07D 319/12 |
| WO | 2012/110117 A1 | 8/2012 | |
| WO | 2013/093028 A1 | 6/2013 | |

OTHER PUBLICATIONS

Dai, J.-Y., "Separation of bio-based chemicals from fermentation broths by salting-out extraction." Engineering in Life Sciences 14.2 (2014): 108-117.*
Fu, H., "Salting-out extraction of carboxylic acids." Separation and Purification Technology 139 (2015): 36-42.*
WO 0043381 A1 WIPO English machine translation (Jan. 8, 2018) p. 1-16.*
Mar. 24, 2016 International Search Report issued in International Patent Application No. PCT/EP2016/052888.
Mar. 24, 2016 Written Opinion of the International Searching Authority issued in International Patent Application No. PCT/EP2016/052888.
Jun. 29, 2018 Office Action issued in Korean Application No. 10-2017-7025068.

* cited by examiner

*Primary Examiner* — John M Mauro
(74) *Attorney, Agent, or Firm* — Oliff PLC

(57) ABSTRACT

A method for producing lactide including the steps of: providing a solution of lactic acid in a volatile organic solvent, subjecting the solution to an evaporation step to remove volatile organic solvent and water, resulting in the formation of a composition including lactic acid oligomer, adding catalyst to the composition including lactic acid oligomer, and bringing the mixture to reaction conditions, to form lactide. It has been found that the process results in the efficient production of lactide with a high production rate and a good product quality.

15 Claims, 1 Drawing Sheet

METHOD FOR MANUFACTURING LACTIDE

The present invention pertains to a method for manufacturing lactide.

Lactide is well known in the art as a starting material for polylactide polymer, which is also indicated as polylactic acid, or PLA. PLA is used in medical applications, for example in biodegradable sutures, clamps, bone plates, and biologically active controlled release devices. Additionally, PLA is an attractive polymer for many applications, e.g., in packaging, because it is biodegradable, and can be obtained from renewable resources.

Conventionally, lactide is manufactured from lactic acid by a process comprising the steps of polymerising lactic acid to form lactic acid oligomers, and depolymerising the lactic acid oligomers in the presence of a catalyst, to form lactide. The lactic acid can be obtained from many sources, e.g., by subjecting a hydrocarbon source to a fermentation medium to manufacture lactic acid, followed by isolating the lactic acid.

To make PLA an attractive alternative for petroleum-derived polymers, there is need in the art for a method for manufacturing lactide which results in the efficient production of lactide with a high production rate and a good product quality. The present invention provides such a method.

The invention pertains to a method for producing lactide comprising the steps of
  providing a solution of lactic acid in a volatile organic solvent,
  subjecting the solution to an evaporation step to remove volatile organic solvent and water, resulting in the formation of a composition comprising lactic acid oligomer,
  adding catalyst to the composition comprising lactic acid oligomer, and bringing the mixture to reaction conditions, to form lactide.

The process according to the invention has been found to have a number of advantages.

In the first place, starting a lactide manufacturing step from a solution of lactic acid in an organic solvent also has process advantages from the viewpoint of an overall cost-effective lactide production process. This will be elucidated in more detail below. Further, and surprisingly it has been found that synthesising lactide from a solution of lactic acid in a volatile organic solvent actually gives good results, and may even be lead to a higher reaction rate than synthesising lactide from a solution of lactic acid in water.

Figure 1:
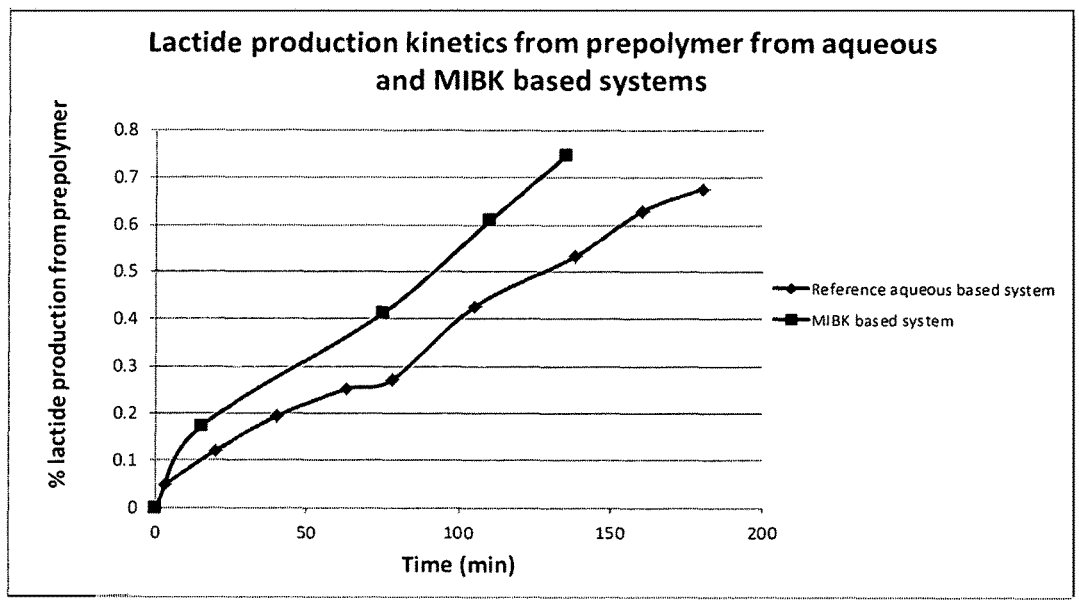
Figure 2:
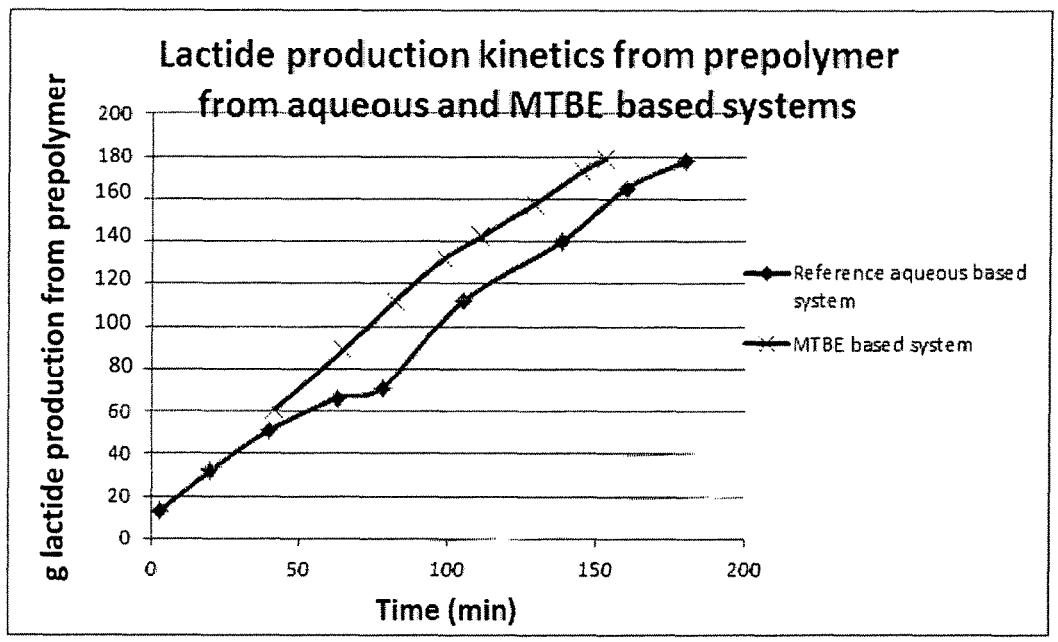

FIGS. 1 and 2 show the percentage of lactide produced from prepolymer over time for the systems of Example 1 (reference aqueous based system) and, respectively, Example 2 (MIBK based system according to the invention) and Example 4 (MTBE based system according to the invention). From FIGS. 1 and 2 it can be seen that the systems according to the invention show a higher reaction rate than the comparative system. This can be used in the configuration of a total process and in equipment design to reduce costs.

As indicated above, the process according to the invention is associated with process advantages. To explain this, a conventional process of manufacturing lactic acid will first be described.

Lactic acid is often manufactured by fermentation. During fermentation, a base is often added to neutralise the lactic acid and keep the pH in a range suitable for the microorganism generating the lactic acid. This results in a fermentation broth comprising a lactic acid salt. The lactic acid salt is typically converted to lactic acid by acidification with a strong inorganic acid. This can be done on the fermentation broth as such, but also after removal of biomass therefrom, and optional further purification steps. The result is an aqueous solution comprising lactic acid, a (dissolved or solid) salt resulting from the acidification step (the cation of the lactate salt and the anion from the acid) and optional further components, such as one or more additional components resulting from the fermentation broth.

There are a number of manners in which the lactic acid can be isolated and purified starting from this aqueous medium.

Examples of these include distillation and extraction. Where an extraction step is used, the fermentation medium, often after various purification steps such as biomass removal, is contacted with an organic solvent, resulting in the formation of a solution of lactic acid in an organic solvent. This solution is conventionally processed in one of two ways. As a first possibility, the solution of lactic acid in an organic solvent is subjected to a back-extraction step, by contacting it with water. This is described, e.g., in WO00/17378, which described the use of amines, alcohols, and ethers, preferably isoamyl alcohol, diisopropylether, and Alamine 336, which is a high-boiling teriary amine with a low solubility in water. WO95/03268 describes extracting a feed containing a carboxylic acid, e.g., lactic acid, with an oxygenated solvent having 4-12 carbon atoms, and having at least one functional group selected from the group consisting of hydroxyl, ester, keto, ether, carbonyl, and amido. The solvent extract is subsequently back extracted with an aqueous liquid. Further, WO2013/093028 describes extraction of lactic acid from an aqueous mixture comprising lactic acid and at least 5 wt. % magnesium chloride, using an organic solvent selected from the group consisting of C5+ ketones, diethylether, and methyl-t-butyl ether. The organic lactic acid solution is subjected to a back-extraction step by contacting it with water, to form an aqueous lactic acid solution. In the process of this reference, the extraction-back-extraction combination makes it possible to obtain a lactic acid product solution which is more concentrated than the lactic acid starting solution.

In addition to back extraction, it has also been described to extract the lactic acid from an aqueous solution using a volatile solvent, and then remove the solvent. For example, U.S. Pat. No. 2,710,880 describes extraction of lactic acid from an aqueous medium comprising lactic acid and a solute salt using alcohols or ketones having 3-4 carbon atoms. In the example, the solvent is removed by distillation. GB173,479 describes an analogous process.

GB280969 describes a process wherein sulphuric acid and sodium sulphate are added to an 80% lactic acid solution, and the solution is extracted with ether. The extract is washed with water to remove contaminants. It is indicated that the ether can be removed in a "well-known manner" and reused.

In the process according to the invention, rather than subjecting the extractant comprising lactic acid to a back extraction step or a distillation step to recover lactic acid, and then convert the lactic acid to lactic acid oligomer, the solution of lactic acid in a volatile organic solvent is used directly as starting material in the manufacture of lactide, which leads to savings both in investment in apparatus, and in processing costs. Additionally, it has been found, and surprisingly, that the process according to the invention leads to lactide formation in good yield, without the formation of undesired side products, and even at a reaction rate which may be increased.

It is noted that US2009/0093034 describes a method for extraction of lactic acid from an fermentation liquor with a pH of 4.8 or less, using a solvent selected from toluene, xylene, mesytylene, ethylbenzene, methanol, ethanol, propanol, butanol, and mineral spirit. It is stated that oligolactic acid can be obtained by heating a lactic acid fermentation medium with a pH of 4.8 or less under reduced pressure, and washing with water. It also describes a process wherein a solvent as described above is added to a fermentation medium, the solvent-containing fermentation medium is heated to a temperature between the azeotrope of the solvent and water and the boiling point of the solvent to form lactic acid oligomers, and heating the fermentation liquor to a temperature ranging from 60° C. to the boiling point of the solvent, to extract the oligolactic acid from the fermentation medium. This reference does not describe, int. al., the direct conversion of the product into lactide.

US2012/0116100 describes a method for the production of hydroxycarboxylic cyclic dimers comprising a depolymerisation step of hydroxycarboxylic acid oligomers wherein in the depolymerisation step a reaction solution is heated via heat transfer from a heating medium passage under reduced pressure while the reaction solution flows through a horizontally provided reaction solution passage. The use of a volatile organic solvent is not described.

US2011/0155557 describes a process for producing lactide from lactic acid oligomers which includes the step of heating the lactic acid oligomer in the presence of a catalyst at a temperature between 150 and 300° C. The use of a volatile organic solvent is not described.

WO2012/110117 describes a method for manufacturing a polyhydroxycarboxylic acid, specifically a polylactic acid via a ring opening polymerisation process using lactide as starting material. Lactide is removed from the polymer product, and recycled to the start of the reaction.

Manufacturing lactide through a process comprising the use of a volatile organic solvent is not described.

U.S. Pat. No. 5,420,304 describes an integrated process for the manufacture of cyclic esters via a sequential extraction/reaction process using multiple solvents. Formation of a lactic acid oligomer by evaporation of volatile organic solvent and water, followed by the addition of a catalyst to form lactide is not described.

The invention and its various embodiments will be described in more detail below.

A first step in the process according to the invention is the provision of a solution of lactic acid in a volatile organic solvent.

Within the context of the present invention, an organic solvent is volatile when it has a boiling point at atmospheric pressure which is below 200° C. For a solvent to be suitable for use in the present invention, it is required that it does not react with the lactic acid under conditions that will be encountered in the process according to the invention. Therefore, the solvent should not comprise alcohols in substantial amounts, as these may react with lactic acid under the formation of lactic acid esters. Also the solvent should not comprise amines in substantial amounts, as these may react to form lactic acid amides.

It is preferred for the solvent to comprise less than 5 wt. % of the total of alcohols and amines, more in particular less than 2 wt. %, still more in particular less than 1 wt. %.

It is further preferred for the solvent not to contain substantial amounts of esters, as they may hydrolyse. It is therefore preferred for the solvent to comprise less than 5 wt. % of esters, more in particular less than 2 wt. %, still more in particular less than 1 wt. %.

Further, it is preferred for the solvent to be used in the present invention to have a relatively high solubility for lactic acid. This allows the preparation of a solution of lactic acid in the solvent of a relatively high concentration, e.g., at least 5 wt. %, more in particular at least 10 wt. %. Otherwise, the use of very high solvent volumes will be required. For this reason, the use of straight chain alkanes is considered less suitable, and the same goes for aromatic compounds like toluene, xylene, mesytylene, and ethylbenzene. Preferred solvents for use in the present invention are those selected from the group comprising C2-C10 ketones and C2-C10 ethers.

Particularly preferred solvents for use in the present invention are those selected from the group comprising C2-C8 ketones and C2-C6 ethers. The use of methyl-isobutyl ketone, methyl-ethyl ketone, and 2- or 3-pentanone has been found to be particularly attractive.

Mixtures of compounds can also be used.

As indicated above, the solution of lactic acid in a volatile organic solvent preferably has a lactic acid concentration of at least 5 wt. %, in particular at least 10 wt. %. There is no maximum to the lactic acid concentration, as the solvent will be evaporated anyway. A higher lactic acid concentration, and thus a lower solvent content will require less solvent evaporation, which will be attractive from a commercial point of view. From a practical point of view, the lactic acid concentration will generally be below 40 wt. %.

The solution of lactic acid in a volatile organic solvent may contain further components. In particular, it may contain water, especially if it is derived from an extraction process. As water will have to be removed for lactide production, it is preferred for the water content to be relatively low. In particular, it is preferred for the water content of the solution of lactic acid in a volatile organic solvent to be below 15 wt. %.

In one embodiment, the solution of lactic acid in a volatile organic solvent is obtained by extracting lactic acid from an aqueous medium, by contacting an aqueous medium with the organic solvent, and subjecting the thus obtained reaction medium to a liquid-liquid separation step. This will be discussed in more detail further on in the specification.

The solution of lactic acid in a volatile organic solvent is subjected to an evaporation step to remove organic solvent and water, resulting in the formation of a composition comprising lactic acid oligomer.

The evaporation step can be carried out using methods known in the art. It can, e.g., be carried out at increased temperature at atmospheric pressure, or at reduced pressure. The advantage of working at reduced pressure is that lower temperatures can be applied. The use of lower temperatures may be attractive to reduce the racemisation of lactic acid.

The evaporation step results in the formation of a composition comprising lactic acid oligomer. The lactic acid oligomers generally have an average degree of polymerisation of between 2 and 30, in particular between 4 and 20, more in particular between 5 and 15. It is believed that with an average degree of polymerisation in this range a balance has been found between limiting the amount of volatile low-molecular weight oligomers on the one hand, and on the other hand keeping the viscosity at acceptable levels by limiting the amount of very high molecular weight oligomers. In the context of the present specification the average degree of polymerisation is defined as follows:

$$DP=1+(1000/(FA*10/90)-90)/72$$

In this formula, DP stands for the average degree of polymerisation and FA stands for the free acid content in wt % as determined through titration.

The composition may further contain a residual amount of solvent, e.g., in the range of 0 to 5 wt. %, more specifically in the range of 0 to 2 wt. %, more specifically in the range of 0-0.5 wt. %.

The composition may further comprise water, e.g., in the range of 0 to 5 wt. %, more specifically in the range of 0 to 2 wt. %, still more specifically in the range of 0-0.5 wt. %.

To the composition comprising lactic acid oligomer, a catalyst is added, which catalyses the depolymerisation/cyclisation process wherein lactic acid oligomers are converted into lactide. Suitable catalysts are known in the art and include metal oxides, metal halides, metal dusts, organic metal compounds derived from carboxylic acids or the like, and organic compounds like guanidine. The use of a catalyst comprising tin(II) is considered preferred. The catalyst may, e.g., comprise tin(II) oxide or tin(II)-2-ethylhexanoate, which is well known in the art for this purpose. The catalyst may, e.g., be added in an amount of 0.01 to 5 wt. %, in particular in an amount of 0.01 to 2 wt %, calculated on the amount of lactic acid oligomer.

The reaction mixture is then brought to reaction conditions to form lactide. Suitable reaction conditions include a temperature in the range of 160 to 220° C., more in particular in the range of 180 to 200° C., and a pressure in the range of 1 to 15 mbar. Upon formation the lactide evaporates, and may be collected, e.g., by condensing in a condenser. Higher-boiling lactic acid oligomers do not evaporate. Hence, it is possible to obtain lactide in high purity.

The lactide obtained by the process according to the invention can be further processed by methods known in the art. Depending on the envisaged future use, purification steps such as crystallisation or distillation may be desirable.

Lactide (sometimes also referred to as dilactide) is the cyclic dimer of lactic acid. Lactic acid exists in two forms which are optical enantiomers, designated as D-lactic acid and L-lactic acid. L-lactic acid is the form predominantly occurring in nature, and is the form which is generally obtained in fermentation processes. The existence of two types of lactic acid makes for three types of lactide, depending on whether it consists of two L-lactic acid molecules, two D-lactic acid molecules or an L-lactic acid molecule and a D-lactic acid molecule combined to form the dimer. These three dimers are designated. respectively, L-lactide, D-lactide, and meso-lactide. In addition, a 50/50 mixture of L-lactide and D-lactide with a melting point of about 126° C. is often referred to in literature as D,L-lactide.

The optical activity of lactic acid and lactide are known to alter under certain conditions, tending towards equilibrium at optical inactivity, where equal amounts of the D and L enantiomers are present. Relative concentrations of D and L enantiomers in the starting materials, the presence of impurities or catalysts and time at varying temperatures, and pressures are known to affect the rate of such racemization. The optical purity of the lactic acid or the lactide is decisive for the stereochemistry of the polylactic acid obtained upon ring-opening polymerization of the lactide, and a key parameter for polymer properties.

It has been found that in the process of the invention the optical purity of the starting material can be retained to a relatively large degree. In other words, if the process according to the invention starts out with lactic acid with an optical purity of at least 90%, in particular at least 95%, more in particular at least 98.5%, even more in particular at least 99.5%, a lactide vapor is obtained from the reaction mixture with an optical purity of at least 85%, in particular at least 92%, more in particular at least 97.5%, even more in particular at least 99%. The loss in optical purity preferably is less than 5%, in particular less than 3%, more in particular less than 1%, even more in particular less than 0.5%, wherein the loss of optical purity is defined as the difference between the optical purity of the starting lactic acid and the optical purity of the lactic acid as present in the lactide as it is present in the lactide vapor obtained from the reaction mixture.

In the present specification, the indication optical purity refers to the percentage of either D-lactic acid or L-lactic acid, calculated on the total amount of lactic acid present in the system. Depending on the stage in the process, the lactic acid will be present in the form of lactic acid, lactic acid oligomer, and/or lactide. An optical purify of 90% thus means that, calculated on the total amount of lactic acid molecules present in the system in whatever form, 90% is L-lactic acid with 10% being D-lactic acid, or 90% is D-lactic acid with 10% being L-lactic acid.

It is preferred for the lactic acid present in the starting material to be L-lactic acid with an optical purity of at least 90%, in particular at least 95%, more in particular at least 98.5%, even more in particular at least 99.5%.

In one embodiment, the solution of lactic acid in a volatile organic solvent used as starting material in the process according to the invention is obtained by extracting lactic acid from an aqueous medium. This extraction step can comprise contacting an aqueous medium comprising lactic acid with a volatile organic solvent which is at least in part not miscible with the aqueous medium comprising lactic acid. For suitable organic solvents, reference is made to what is stated above.

The lactic acid content of the aqueous medium is preferably as high as possible. For example, the aqueous mixture may comprise at least 5 wt. %, preferably at least 10 wt. %, more preferably at least 15 wt. % lactic acid, based on the total weight of the aqueous mixture. Values of at least 20 wt. %, more in particular at least 25 wt. % may be particularly preferred. As a maximum, a value of 40 wt. % may be mentioned.

In one embodiment, the aqueous mixture has a pH of 2 or lower, typically a pH below 1, for example a pH of 0-1. It is preferred for the pH to be relatively low, to ensure that the lactic acid is present in the mixture in acidic form, allowing extraction. The pH may be adapted by the addition of an inorganic acid.

In one embodiment, the aqueous medium comprising lactic acid comprises at least 5 wt. % of a dissolved inorganic salt. It has been found that the presence of a dissolved inorganic salt results in an improved extraction process, in that a larger amount of lactic acid is incorporated into the volatile organic solvent. Further, the presence of a dissolved inorganic salt means that the solubility of the organic solvent in the aqueous medium decreases. This leads to less solvent loss during the extraction process, which is attractive from both an economical and an environmental point of view. Further, the solubility of water in the organic solvent also decreases at increasing salt concentrations. These combined effects result in the potential application of solvents that are miscible with pure water, but only partially miscible with water comprising a substantial amount of salt. This leads to a broader range of possible suitable solvents. To increase the effect of the invention, the salt concentration preferably is relatively high. It may be preferred for the salt concentration to be at least 10 wt. % more preferably at least 15 wt. %, even more preferably at least 20 wt. %. Depending on the lactic acid content of the solution, the salt content may be higher, e.g., at least 25 wt. %, or at least 30 wt. %, or sometimes at least 35 wt. %. The maximum value is generally determined by the solubility of the salt in question in the lactic acid solution in question, and can easily be determined by the skilled person.

Suitable inorganic salts for use in the present invention are inorganic salts with a high solubility in water, in particular a solubility which allows obtaining the salt concentrations specified above. The cations present in the inorganic salt preferably is selected from the group consisting of magnesium, calcium, potassium, sodium, nickel, cobalt, iron and aluminium, and ammonium, and combinations thereof. The use of one or more cations selected from the group of magnesium, calcium, sodium, and potassium is preferred. The use of calcium and magnesium is particularly preferred, as these cations have been found to promote the presence of lactic acid in the organic phase. The use of magnesium may be especially preferred for this reason.

The anion of the inorganic salt can, e.g., be selected from nitrate, sulphate, and halide. It will be evident to the skilled person that anion and cation should be matched in such a manner that a soluble salt is obtained. The use of halide salts may be preferred from a practical point of view. The halide salt may be a fluoride, chloride, bromide, or iodide. The use of chloride is preferred. This selection applies in combination with the preference for the cations specified above. Specific examples of preferred salts are $MgCl_2$, $CaCl_2$, NaCl, and KCl. It was found that these salts contribute to an increased distribution of the lactic acid to the organic phase. The use of calcium and magnesium chloride is considered preferred. The use of magnesium chloride may be particularly preferred.

In the extraction step, the aqueous medium comprising lactic acid, and preferably dissolved inorganic salt as described above, is combined with the organic solvent, generally under such conditions that an intense contact between the solvent and the medium is ensured. A system is formed comprising an aqueous phase, which, if present, contains the soluble salt and possibly some remaining lactic acid, and an organic solvent phase, which comprises lactic acid.

The separation step, wherein the aqueous phase and the organic solvent phase are separated from each other via liquid-liquid separation can be done using methods known in the art for separating a liquid-liquid two-phase system. Examples of suitable apparatus and methods for liquid-liquid separation include decantation, settling, centrifugation, use of plate separators, use of coalescers, and use of hydrocyclones. Combination of different methods and apparatus may also be used.

The separation step may be carried out at any suitable temperature, in general in the range of 5-95° C. For the composition of the solvent phase, reference is made to what is stated above.

In one embodiment, the aqueous medium comprising lactic acid, and preferably dissolved inorganic salt, is obtained by a process encompassing an acidification step comprising adding an inorganic acid to a lactic acid salt, to provide an aqueous medium liquid comprising lactic acid and a dissolved inorganic salt.

The lactic acid salt may be in solid form, e.g., in the form of a filter cake or suspension. This can be the case where the lactate salt has a relatively limited solubility in water, e.g., in the case of magnesium lactate. On the other hand, the lactic acid salt may also be provided in dissolved form, e.g., for sodium lactate, potassium lactate, and calcium lactate.

The acid used in the acidification step, also indicated as acidulation step, typically is a strong acid, such as hydrochloric acid, sulfuric acid, or nitric acid. The acid should be selected in such a manner that the anion of the acid and the cation of the latate salt together form a soluble salt. The use of hydrochloric acid or nitric acid is preferred, with the use of hydrochloric acid being particularly preferred. In this case, an aqueous mixture is obtained comprising lactic acid and a chloride salt. In a preferred embodiment, magnesium lactate in solid form is contacted with a hydrochloric acid solution, resulting in the formation of an aqueous medium comprising lactic acid and dissolved magnesium lactate.

Acidulation may for example be conducted by bringing the lactate salt, in silid or dissolved form, in contact with an aqueous acid solution. In the case of HCl, which can also be in gaseous form, it is also possible to bring a lactate salt solution or suspension in contact with a gas stream comprising HCl.

When acidulation of the lactate salt is conducted by contacting it with an acidic solution, it preferably has an acid concentration as high as possible. Such a high acid concentration will result in an aqueous mixture with a high lactic acid concentration, which is desirable. The acidic solution therefore comprises at least 5 wt. %, more preferably at least 10 wt. % and even more preferably at least 20 wt. % acid, based on the total weight of the acidic solution. Acidulation is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case a gas stream comprising HCl is used, a lactate solution or suspension may be contacted with the gas stream comprising HCl, e.g., by blowing it through the lactate solution or suspension. In case HCl gas is used, the HCl may originate from a thermal decomposition step, as described above.

Preferably, acidulation is conducted at a temperature of 75° C. or less. At higher temperatures, it becomes uneconomical to adapt equipment to the harsh conditions of an acidic environment at high temperatures.

After acidulation, solid material, if present, may be removed from the aqueous mixture, for example by filtration. The presence of solid material in the aqueous mixture in not desirable during extraction.

The aqueous mixture may be concentrated after acidulation prior to extraction to a concentration up to the solubility of the inorganic soluble salt.

In one embodiment, a lactate salt, in particular calium lactate, sodium lactate, potassium lactate, or magnesium lactate, in particular magnesium lactate is used which originates from a fermentation process. Accordingly, the method of the invention may further comprise a fermentation step to form the lactic acid, which fermentation process comprises the steps of fermenting a carbon source, such as a carbohydrate, by means of a micro-organism in a fermentation broth to form lactic acid and neutralizing at least part of the lactic acid by addition of a base, in particular a sodium base, potassium base, calcium base, or magnesium base, more in particular a magnesium base, thereby obtaining a lactate salt as specified above, in particular magnesium lactate.

Fermentation processes for the manufacture of lactic acid are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising a lactate salt, biomass, and optionally further components, such as impurities like sugars, proteins, and salts. The lactate salt may be present in solid form, in dissolved form, or both in solid form and in dissolved form. For example, sodium lactate, potassium lactate, and calcium lactate are generally present in the dissolved form. Magnesium lactate is often present both in the solid form and in the dissolved form, depending on concentration.

If so desired, the fermentation broth may be subjected to a biomass removal step, e.g., a filtration step, before further processing. This is generally preferred for improving product quality, in particular product color.

Another intermediate step may be separation of solid reaction product, e.g., magnesium lactate, from the fermentation broth, before, after, or simultaneous with biomass removal, and optionally subjecting the solid product, e.g., magnesium lactate, to a washing step. Depending on the concentration, magnesium lactate can precipitate in the fermentation medium. In one embodiment, the solid magnesium lactate is separated from the fermentation medium, e.g., by filtration, and subjected to an acidification step as described above.

Another intermediate step may be subjecting the fermentation broth to a concentration step to increase the concentration of lactate salt in the composition before acidification. This step may be carried out before, after, or simultaneous with biomass removal. Such a step may be attractive to increase the content of solid lactate salt, which may then be separated from the fermentation broth as described above, and processed as solid lactate salt, in particular magnesium lactate in the process according to the invention.

Other intermediate steps, e.g., purification steps, may be carried out as desired, as will be evident to the skilled person.

It will be clear to the skilled person that preferred aspects of various steps in the method according to the invention can be combined as desired.

The invention will be elucidated by the following examples, without being limited thereto or thereby.

EXAMPLE 1 (COMPARATIVE)

4520 g of 9 wt. % lactic acid solution in water was prepared. This solution was concentrated to approximately 90 wt. % at pressure 100 mbar(a). After the concentration there was 480 g of concentrated lactic acid solution. 400 g of concentrated lactic acid solution was heated in 90 min in a round bottom flask using a mechanical stirrer to the set point of 180° C. and slowly vacuum was applied. In 90 minutes the pressure was decreased to 100 mbar(a) while water was evaporating. Then the pressure was decreased in the next 60 min further to 50 mbar(a) and eventually to 40 mbar(a). In total 94 g of water was condensed.

The prepolymer in the flask thus produced had a free acid content of 17 wt %, as measured by titration. From this number it can be calculated that the average degree of polymerization of the prepolymer was 7.1. A HPLC measurement showed that the prepolymer comprised 4.1 wt. % of the total of D and L lactide and less than 0.1 wt. % mesolactide. The water content of the prepolymer was 0.24 wt % as measured with a Karl Fischer titration.

The lactide synthesis was performed directly after the pre-polymerisation step in the same reactor. First 0.05 wt. % of tin 2-ethylhexanoate (catalyst) was added. The content of the flask, with pre-polymer (263 g) was heated to 120° C. before the stirrer was started due to very high viscosity. The set point was then increased to 200° C. Then the vacuum was decreased to 10 mbar(a). 192 g of lactide was evaporated and condensed in 3.25 hours.

The resulting lactide comprised 87.8 wt. % of the total of D and L lactide, and 3.3 wt. % mesolactide, as measured by a HPLC method. The HPLC further showed that the remainder of components was mainly lactic acid, lactoyllactic acid, and lactoyllactoyllactic acid. These components are liberated through the catalyst progressively cleaving off lactide from even and uneven oligomers, and while having a boiling point in the same range as lactide, they are evaporated along with lactide.

EXAMPLE 2 (ACCORDING TO THE INVENTION)—MIBK AS SOLVENT 3977 g of 10 wt. % lactic acid solution in methyl isobutyl ketone (MIBK) containing 2% of water was prepared. This solution was concentrated to approximately 90 wt. %. at 90° C. and pressure 120 mbar(a). After the concentration there was 439 g of concentrated lactic acid solution. 420 g of concentrated lactic acid solution was heated in 50 min in a round bottom flask using a mechanical stirrer to the set point of 180° C. and slowly vacuum was applied. In 60 minutes the pressure was decreased to 100 mbar(a) while water and MIBK were still evaporating. When 100 mbar(a) was reached almost no MIBK was coming over to the condensate which indicates that (almost) all MIBK was evaporated. Then the pressure was decreased in the next 30 min further to 50 mbar(a) and only 2 ml of the condensate was collected.

In total 117 g of water/MIBK was condensed. The free acid content was measured by titration to be 12.2 wt %, leading to an average degree of polymerisation of 10.

The prepolymer comprised 5.2 wt. % of the total of D and L lactide and less than 0.5 wt. % mesolactide, as measured by HPLC. The water content in the prepolymer was measured to be 0.43 wt % by a Karl Fischer titration.

The lactide synthesis was performed directly after the pre-polymerisation step in the same reactor, with 296 g prepolymer. First 0.05 wt. % of tin 2-ethylhexanoate (catalyst) was added. The content of the flask, with pre-polymer was heated to 200° C. Then the vacuum was decreased to 10 mbar(a). 197 g of lactide was evaporated and condensed in 2.25 hours. The resulting lactide comprised of 87.3 wt. % of the total of D and L lactide, and 1.5 wt. % mesolactide, the remainder being lactic acid and higher oligomers.

FIG. 1 shows the weight of lactide produced from prepolymer over time for the systems of Example 1 (reference aqueous based system) and Example 2 (MIBK based system according to the invention). From FIG. 1 it can be seen that the system according to the invention shows a higher reaction rate than the comparative system. This can be used in the configuration of a total process and in equipment design to reduce costs.

EXAMPLE 3 (ACCORDING TO THE INVENTION)—2-PENTANONE AS SOLVENT

A solution of 2096.6 g of 20 wt % lactic acid (lactic acid crystals, Purac Corbion) in 2-pentanone (Acros) containing 2 wt % of water was prepared. This solution was concentrated to approximately 90 wt % at 80-90° C. at reduced pressure in a rotavap (1589.3 g water and 2-pentanone condensed). After the concentration there was 449 g of concentrated lactic acid solution. The solution was transferred to a round-bottom flask with a mechanical stirrer and was heated in 55 minutes to 180° C. At 180° C. slowly vacuum was applied down to 100 mbar. In 60 minutes water and 2-pentanone were further evaporated and a two phase system was formed in the condenser cooled at room temperature. After 100 mbar was reached the pressure was further reduced to 50 mbar to the point that some lactide present at equilibrium in the prepolymer started to evaporate, and crystallise in the condenser.

In total 116 g of water/2-pentanone was condensed, of which 56 g as the aqueous phase. Based on all weights, it was estimated that a pre-polymer with an average degree of polymerization of 7-8 was made. The prepolymer comprised 4.7 wt. % of the total of D and L lactide and 0.4 wt. % mesolactide.

Next 0.05 wt % of tin 2-ethylhexanoate (catalyst) was added. The prepolymer (315 g) was heated to 200° C., and the vacuum reduced slowly to 10 mbar. In 160 minutes 157.3 g of lactide was distilled off, faster than the reference. The lactide had a content of D+L lactide of 68.3 wt %. This lower purity than the reference and MIBK case, indicate the relatively low DP of the prepolymer, and co-distillation of lactic acid and lactoyllactic acid liberated by depolymerisation of prepolymer by the catalyst. Through optimization the temperature-pressure relationship during prepolymerisation the DP of the prepolymer and consequently the purity of the lactide can be increased. The meso-lactide content of the lactide was 0.9 wt %.

EXAMPLE 4 (ACCORDING TO THE INVENTION)—MTBE AS SOLVENT

A solution of 3505.9 g of 12 wt % lactic acid (lactic acid crystals, Purac Corbion) in MTBE (methyl tertiair-butyl ether, Acros) containing 4 wt % of water was prepared. This solution was concentrated to approximately 90 wt %. at 80-90° C. at reduced pressure in a rotavap (3040.3 water and MTBE condensed). After the concentration there was 434.9 g of concentrated lactic acid solution. The solution was transferred to a round-bottom flask with a mechanical stirrer and was heated in 101 minutes to the set point 180° C. At 180° C. slowly vacuum was applied down to 80 mbar in 23 minutes, while water and MTBE were further evaporating. At 80 mbar some lactide present at equilibrium in the prepolymer started to evaporate, and crystallise in the condenser, and prepolyemrisation was stopped. In total 110 g of water and MTBE was evaporated. It was estimated that a pre-polymer with an average degree of polymerization of 7-8 was made.

The prepolymer comprised 4.7 wt. % of the total of D and L lactide and 0.4 wt. % mesolactide.

Next 0.05 wt % of tin 2-ethylhexanoate (catalyst) was added.

The prepolymer (316 g) was heated to 200° C., and the vacuum reduced slowly to 5 mbar. In 153 minutes 180 g of lactide was distilled off, faster than the reference. The lactide had a content of D+L lactide of 77 wt %. The meso-lactide content of the lactide was 1.1 wt %.

FIG. 2 shows the weight of lactide produced from prepolymer over time for the systems of Example 1 (reference aqueous based system) and Example 4 (MTBE based system according to the invention). From FIG. 2 it can be seen that the system according to the invention shows a higher reaction rate than the comparative system. This can be used in the configuration of a total process and in equipment design to reduce costs.

EXAMPLE 5 (ACCORDING TO THE INVENTION)—MEK AS SOLVENT

A solution of 1680 g of 25 wt % lactic acid (lactic acid crystals, Purac Corbion) in MEK (methyl ethyl ketone, Acros) containing 10 wt % of water was prepared. This solution was concentrated to approximately 90 wt %. at 80° C. at 150 mbar pressure in a rotavap (1217 g water and MEK condensed). After the concentration there was 445.5 g of concentrated lactic acid solution. The solution was transferred to a round-bottom flask with a mechanical stirrer and was heated in 81 minutes to the set point of 180° C. At 180° C. slowly vacuum was applied down to 100 mbar in 60 minutes, while water and MEK were further evaporating. At 100 mbar already some lactide started to evaporate and crystallise in the condenser and prepolymerisation was stopped. In total 94 g of water and MEK was evaporated. It was estimated that a pre-polymer with an average degree of polymerization of 7-8 was made. The prepolymer comprised 3.5 wt % of the total of D and L lactide and less than 0.1 wt. % mesolactide.

Next 0.05 wt % of tin 2-ethylhexanoate (catalyst) was added. The prepolymer was heated to 200° C., and the vacuum reduced slowly to 10 mbar. In 185 minutes 155 g of lactide was distilled off, faster than the reference. The lactide had a content of D+L lactide of 70 wt %. The meso-lactide content of the lactide was 1 wt %.

The invention claimed is:
1. Method for producing lactide comprising the steps of providing a solution of lactic acid in a volatile organic solvent having a lactic acid concentration of at least 5 wt %,
subjecting the solution to an evaporation step to remove volatile organic solvent and water, resulting in the formation of a composition comprising lactic acid oligomer, wherein the total amount of alcohols and amines comprised in the volatile organic solvent of the solution is less than 5 wt %,
adding catalyst to the composition comprising lactic acid oligomer, and bringing the mixture to reaction conditions, to form lactide.
2. Method according to claim 1, wherein the concentration of lactic acid in the solution of lactic acid in a volatile organic solvent is at least 5 wt. % and below 40 wt. %.
3. Method for producing lactide comprising the steps of:
providing a solution of lactic acid in a volatile organic solvent,
subjecting the solution to an evaporation step to remove volatile organic solvent and water, resulting in the formation of a composition comprising lactic acid oligomer,
adding catalyst to the composition comprising lactic acid oligomer, and bringing the mixture to reaction conditions, to form lactide, wherein
the volatile organic solvent of the solution comprises one or more member selected from C2-C10 ketones, and C2-C10 ethers.
4. Method according to claim 1, wherein the water content of the solution is below 15 wt. %.
5. Method according to claim 1, wherein in the composition comprising lactic acid oligomer, the lactic acid oligomers have an average degree of polymerisation of between 2 and 30.

6. Method according to claim 1, wherein
the composition comprising lactic acid oligomers formed after the evaporation step comprises a residual amount of solvent in the range of 0 to 5 wt. % and/or water in the range of 0 to 5 wt. %.

7. Method according to claim 1, wherein the reaction conditions during the lactide formation step include a temperature in the range of 160 to 220° C. and a pressure in the range of 1 to 15 mbar.

8. Method according to claim 1 wherein the lactic acid in the starting solution has an optical purity of at least 90%, and wherein a lactide vapour is obtained with an optical purity of at least 85%.

9. Method according to claim 1 wherein the loss in optical purity of the lactic acid during the lactide formation reaction is less than 5%.

10. Method according to claim 1 wherein the solution is obtained by extracting lactic acid from an aqueous medium.

11. Method according to claim 10, wherein the aqueous medium comprises lactic acid and at least 5 wt. % of a dissolved inorganic salt.

12. Method according to claim 11, wherein the aqueous medium comprising the lactic acid and the dissolved inorganic salt is obtained by a process including an acidification step comprising adding an inorganic acid to a lactic acid salt.

13. Method according to claim 12, wherein the lactic acid salt is selected from the group consisting of magnesium lactate, calcium lactate, sodium lactate, and potassium lactate.

14. Method according to claim 12, wherein
the inorganic acid is selected from the group consisting of hydrochloric acid, nitric acid, and sulphuric acid, wherein the acid is selected such that the anion of the acid and the cation of the lactate salt together form a soluble salt.

15. Method according to claim 12, wherein the solution of a lactic acid salt is derived from a fermentation process.

* * * * *